(12) United States Patent
Baron et al.

(10) Patent No.: US 6,949,255 B2
(45) Date of Patent: Sep. 27, 2005

(54) INHIBITORY CHEMICAL FORMULATION WITH PRESERVATIVE SYSTEM

(75) Inventors: Samuel Baron, Dickinson, TX (US); Miles W. Cloyd, Galveston, TX (US); Joyce Poast, Friendswood, TX (US); Derrick Nguyen, Galveston, TX (US)

(73) Assignee: Board of Regents, University of Texas, Austin, TX (US)

( * ) Notice: Subject to any disclaimer, the term of this patent is extended or adjusted under 35 U.S.C. 154(b) by 0 days.

(21) Appl. No.: 10/347,147

(22) Filed: Jan. 17, 2003

(65) Prior Publication Data

US 2003/0170294 A1 Sep. 11, 2003

Related U.S. Application Data

(63) Continuation of application No. 09/969,132, filed on Sep. 24, 2001, now abandoned, which is a continuation of application No. 09/494,201, filed on Jan. 28, 2000, now abandoned.

(51) Int. Cl.[7] .......................... A61F 13/00; A61F 6/06; A61F 9/02; A61K 9/00
(52) U.S. Cl. ...................... 424/434; 424/430; 424/436; 424/400
(58) Field of Search ................................ 424/400, 430, 424/434, 436, 443, 449

(56) References Cited

U.S. PATENT DOCUMENTS 5,078,706 A * 1/1992 Miyamoto et al. .......... 604/349
5,545,673 A * 8/1996 Kelly ...................... 514/772.3

FOREIGN PATENT DOCUMENTS

EP        661028    *  5/1995
EP        661 028 A1   7/1995

OTHER PUBLICATIONS

Price, Joyce Howard, Washington Times Article, p. 3, Nov. 16, 2001.

Mitsuya, et al., "Suramin protection of T cells in vitro against infectivity and cytopathic effect of HTLV–III", Science vol. 226, pp. 172–174 (1984).

Sandstrom, "Antiviral therapy in AIDS, clinical pharmacology properties and therapeutic experience to date", Drugs vol. 34, pp. 372–390 (1987).

Chomienne, et al., "Discrepancy between in vitro and in vivo passaged U–937 human leukemic cells: Tumerorigenicity and sensitivity to differentiating drugs", In Vivo (1998).

* cited by examiner

Primary Examiner—Thurman K. Page
Assistant Examiner—Humera N. Sheikh
(74) Attorney, Agent, or Firm—Harris F. Brotman; Gordon & Rees LLP (57) ABSTRACT

The present invention provides methods for preventing the transmission of HIV, methods for prophylaxis of HIV transmission and methods for reducing the risk of HIV transmission vaginally or rectally using compositions having at least one of polyquaternium, glycerin, methylparaben or proplyparaben. The invention further provides methods for inhibiting the transmission of a sexually transmitted disease using the compositions. Additionally, the invention provides combinations of compositions and devices used with such methods.

7 Claims, 6 Drawing Sheets

INHIBITORY CHEMICAL FORMULATION WITH PRESERVATIVE SYSTEM

This is a continuation application of prior application Ser. No. 09/969,132, filed on Sep. 24, 2001 now abandoned, which is a continuation of U.S. patent application Ser. No. 09/494,201, filed Jan. 28, 2000, now abandoned.

BACKGROUND OF THE INVENTION

1. Field of the Invention

This invention relates generally to methods for prophylaxis against diseases transmittable by sexual contact and more particularly to methods for prophylaxis of HIV transmission. The invention also relates to combinations of compositions and devices used with such methods.

2. Background Information

The need to develop simple, effective and low cost methods to prevent HIV transmission between individuals is an important strategy to manage HIV infection. Recent developments that have identified new more virulent strains of HIV, coupled with the suggestion that certain current therapies may be less effective than they were in the past, have heightened the need to develop methods to circumvent primary HIV infection from sexual contact.

In addition to HIV, many diverse diseases are transmitted sexually. Among the more common are condylomata acuminata (veneral warts), gonorrhea, syphilis, herpes simplex, granuloma cenereum, chancroid, granuloma inguinale, non-gonococcal urethritis, acute pelvic inflammatory disease, vaginitis and anorectal disease.

Although several methods for prophylaxis of these diseases are known, no universally satisfactory method has been developed. In theory, the best way to prevent transmission is abstinence, but in reality this is often impractical and not followed. Other methods involve the insertion of physical barriers to prevent the direct contact of bodily fluid between individuals. However, such methods are often inconvenient, requiring user acquiescence. Moreover, the barriers themselves sometimes fail, negating any potential prophylactic benefits.

More targeted prophylactic methods involve destroying HIV itself so that it is incapable of invading the recipient tissue. Such methods involve the administration of biologically active materials to the vagina, for example. Nonoxynol-9® is known to have bacteriocidal action and to be capable of destroying HIV. However, the use of Nonoxynol-9® and other spermicidal and bacteriocidal agents in vaginally inserted suppositories, creams, foams or the like, are discouraged because of the risk of causing mucosal inflammation. In addition, these agents tend to destroy the healthy bacterial flora of the vagina and often lead to yeast infections. Specifically, the use of Nonoxynol-9® has been reported to result in an increased risk of HIV infection among prostitutes. Kreiss et al., JAMA 268(4) :477–482 (1992), which is incorporated by reference herein.

Other methods to destroy HIV in seminal fluid involve the use of antiseptics containing iodine, for example. (U.S. Pat. No. 5,545,401). However, such methods often require vigilance by the user to ensure that irritation does not result. Another method employs the use of zinc salt containing genital lubricants, in which the user spreads the lubricant on a genital surface to create an anti-viral chemical barrier. (U.S. Pat. No. 5,624,675). However, some individuals may choose not to use such a method due to the uncertain effects that zinc may have upon entry into the bloodstream.

It has been observed that HIV is relatively rarely transmitted by oral secretions. In fact, the saliva of viremic individuals usually contains only noninfectous components of HIV indicating virus breakdown. This has been reported to be due to hypotonic disruption by which saliva kills infected mononuclear leukocytes and prevents their attachment to mucosal epithelial cells and production of infectious HIV. (Baron et al., Arch. Intern. Med. 159:303–310 (1999)). Although saliva could be used as a method for prevention of HIV transmission in oral, vaginal and rectal intercourse, the hypotonic preventative effect of saliva would be negated by the relatively larger quantity of isotonic semen.

Thus, there exists a need for less irritating substances which prevent the transmission of sexually transmitted diseases, as well as the transmission of HIV-infected leukocytes in seminal fluid or HIV in free form. In addition, there is a need for a method in which the preventative properties of the substances remain intact relative to the volume of semen typically introduced. Finally, there is a need for methods for prophylaxis which are simple and convenient to use both vaginally and rectally. The present invention satisfies these needs and provides related advantages as well.

SUMMARY OF THE INVENTION

The present invention provides a method for preventing the transmission of HIV vaginally or rectally by contacting a bodily fluid suspected of containing HIV with a composition having at least one of polyquaternium, glycerin, and a preservative system. An embodiment of the preservative system in this method and those enumerated below comprises methylparaben and proplyparaben.

The invention also provides a method for prophylaxis of HIV transmission vaginally or rectally by contacting a bodily fluid suspected of containing HIV with a composition having at least one of polyquaternium, glycerin, and a preservative system.

The invention also provides a method for reducing the risk of transmission of HIV vaginally or rectally by contacting a bodily fluid suspected of containing HIV with a composition having at least one of polyquaternium, glycerin, and a preservative system.

Further, the invention provides a method for inhibiting the transmission of a sexually transmitted disease caused by an agent that is present in a bodily fluid by placing a composition having at least one of polyquaternium, glycerin, and a preservative system in a vagina, rectum, condom or on some other barrier device that can be inserted into a vagina or rectum prior to deposition of the bodily fluid into the vagina or rectum.

DETAILED DESCRIPTION OF THE INVENTION

The present invention relates to methods for preventing the transmission of HIV, methods for prophylaxis of HIV transmission, methods for reducing the risk of transmission of HIV vaginally or rectally and to methods for inhibiting the transmission of sexually transmitted diseases in general. The methods involve the use of a composition that has at least one of the following components in an aqueous solution: polyquaternium, glycerin, and a preservative system.

Despite extensive public awareness campaigns, the incidence of HIV infection remains high, especially in developing countries. Therefore, to prevent HIV transmission vaginally and rectally, substances are needed that are easy to use, effective and low cost. One formulation of the present invention comprises a sexual lubricant. As such, the chances of it being used, as opposed to barrier devices, such as condoms, are greater. In addition, compositions of the invention are relatively inexpensive to produce.

As used herein, the term "barrier device" refers to a device that serves to physically keep one individual's bodily fluid from coming into contact with another individual. Examples of such devices include, condoms, female condoms, and can also include cervical caps and sponges. Also as used herein, the term bodily fluid refers to a fluid or exudate of an individual that emanates, is expelled or released from the body. Examples of such bodily fluids include, blood, saliva, tears, semen, vaginal discharge, pus, mucous, urine and feces. Such bodily fluids can come into contact with a different individual thereby transmitting sexually transmitted diseases. A bodily fluid may contain HIV in free form or HIV-infected cells.

Infected mononuclear leukocytes are the major infectious component of a donor-carrier's seminal fluid. In addition, they routinely survive in the isotonic seminal fluid in the recipients vagina. The infected mononuclear leukocytes then penetrate the vaginal epithelium and transmit infection to subepithelial leukocytes or attach to and infect CD4-negative epithelial cells. (Milman et al., *AIDS Res. Hum. Retrov.* 10:1305–1312 (1994), which is incorporated herein by reference). It is believed that an infected HIV-leukocyte or a cell-free HIV particle can remain in the vagina or rectum for approximately one-half hour before penetration of the epithelial tissues takes place(Bomsel, M. Nature Medicine, 1997, 3:42–47). Accordingly, the composition of the present invention ideally should be placed in contact with the donor bodily fluid within this one hour time period. Most preferably, the composition will be placed in the vagina or rectum, or even on the penis, before the commencement of sexual contact. Also as used herein, the term "sexual contact" refers to the deposition of an individual's bodily fluid onto or into another individual's mucosal surface or surfaces.

The compositions of the methods of the invention include at least two commercially available vaginal lubricant products: AstroGlide® (BioFilm, Vista, Calif.) and Vagisil® (Combe Inc., White Plains, N.Y.). The AstroGlide® composition is also sold under the brands Silken Secret®, ViAmor®, and Target®. The AstroGlide® product includes water, glycerin, polyquaternium #33, propylene glycol, methylparaben and propylparaben. Vagisil® comprises polyquaternium #32. Without limitation, other polyquaternium-containing vaginal lubricants, included in the compositions of the method, are Just Between Us® Personal Lubricant (Key West Aloe Co.), CVS® Personal Lubricant (Sun Mar Laboratories), and Ultra Lube® (Super Brands), all of which contain polyquaternium #5. Enhance® Personal Lubricant (The Xandria Collection) contains polyquaternium #7. Also without limitation, non-polyquaternium containing personal lubricants included in the composition of the methods disclosed herein include Replens® Vaginal Moisturizer, K-Y Liquid®, K-Y® Long Lasting Vaginal Moisturizer, K-Y Silk-E® Vaginal Moisturizer, K-Y® Jelly Personal Lubricant, Summer's Eve® Vaginal Moisturizer, Aqua Lube®, and Wet, Light®Personal Lubricant Gel.

A novel aspect of the present invention, which has not been recognized previously is that the compositions herein also prevent or reduce the risk of HIV transmission as well as the transmission of other sexually transmitted diseases. For example, the compositions of the present invention may be used to prevent or reduce the likelihood of transmission of the herpes simplex virus, for example, since its morphology and chemistry are similar to that of HIV. It is understood that viral agents morphologically or chemically similar to HIV are subject to prophylaxis or the transmission-preventative methods of the present invention. It is further understood that the selection of morphologically and chemically similar agents are routine to those skilled in the art (Baron et al., *Medical Microbiology*, 4$^{th}$ ed., Galveston Tex., The University of Texas Medical Branch at Galveston, (1996)). In addition, the inventive methods may be effective with sexually transmitted diseases involving bacterial agents. As used herein, the term "agents" refers to a viral, bacterial or other factor that is the pathogen responsible for the transmission of sexually transmitted disease from one individual to the next. For example, an agent in AIDS is HIV, and an agent in genital herpes is HSV.

Also as used herein, the term "effective amount" refers to an amount or concentration of the composition of the present invention which is used in the methods to produce the intended result. In the case of the present invention, effective amounts are generally anti-HIV effective amounts, which may include amounts of the composition which prevent, reduce or are prophylactic for the sexually transmitted spread of HIV, for example. However, effective amounts can refer to anti-HSV or anti-microbe amounts. One skilled in the art understands that the selection of an effective amount will depend upon which agent is under consideration, and further that such a selection will be routine. Specifically, anti-HIV effective amounts or concentrations are amounts or concentrations of the compositions herein which inhibit the replication, growth and elaboration of HIV. For example, an effective amount of an anti-HIV composition is approximately 0.5 ml or more. A preferable effective amount is 1 ml, however the user would likely use much more than that. Alternatively an effective amount can be in the range of 0.5 ml to greater than 10 ml.

Concentration ranges of polyquaternium useful in the present invention are from 0.1% to 10% by weight. Alternatively, any polyquaternium can be used at any concentration that is non-irritating to the mucosal epithelium. It is contemplated that the polyquaternium used herein is cationic in nature, although polyquaterniums which are anionic or non-ionic also find use n the compositions of the method. The International Cosmetic Ingredient Dictionary and Handbook (7$^{th}$ Edition (1997), Vol. 2, eds. J. A. Wenninqer and G. N. McEwen, publ. The Cosmetic, Toiletry, and Fragrance Association, Wash. D.C.) discloses, without limitation, polyquaterniums (and their commercial sources) that are useful in the compositions of the methods of the invention.

Concentration ranges of glycerol useful in the present invention are from about 5% to about 60% by weight. An example of a concentration range of a preservative system useful in the invention involves methylparaben at 0.03% to 0.3% by weight and propylbaraben at 0.015% to 0.15% by weight.

As used herein, the term "preservative system" refers to a chemical or group of chemicals that act to prevent the contamination or degradation of other components in the composition. For example, methylparaben and propylparaben are used as preservatives herein. Examples of other preservatives useful in the present invention include, but are not limited to, the following FDA approved preservative systems for food, cosmetics, and food preparations:

FOOD PRESERVATIVES

| | |
|---|---|
| Sorbic acid | Thiabendazole |
| Sodium sorbate | Nisin |
| Potassium sorbate | Natamycin |
| Calcium sorbate | Formic acid |
| Benzoic acid | Sodium formate |
| Sodium benzoate | Calcium formate |
| Potassium benzoate | Hexamine |
| Calcium benzoate | Potassium nitrite |
| Ethyl4-hydroxybenzoate | Sodium nitrite |
| Sodium salt | Sodium nitrate |
| Propybaraben | Potassium nitrate |
| Propyl4-hydroxybenzoate | Acetic acid |
| Methylparaben | Potassium acetate |
| Methyl4-hydroxybenzoate | Sodium diacetate, sodium acetate |
| Sulphur dioxides | Ammonium acetate |
| Sodium sulphite | Lactic acid |
| Sodium bisulsulphite | Propionic acid |
| Sodium metabisulphite | Sodium propionate |
| Potassium metabisulphite | Calcium propionate |
| Potassium sulphite | Potassium propionate |
| Calcium sulphite | Carbon dioxide |
| Calcium hydrogen sulphite | |
| Potassium bisulphite | |
| Biphenyl | |
| 2-Hydroxybiphenyl | |
| Sodium biphenyl-2-yl oxide | |

COSMETIC PRESERVATIVES

| | |
|---|---|
| Vitamin A | Methyl Paraben |
| Vitamin C | o-phenyl-phenol |
| Vitamin E (tocopherol) | Propyl Paraben |
| Grapefruit Seed Extract | Ethyl Paraben |
| Gum Benzoin | Isopropyl Myristate |
| Pycnogenol | Isopropyl Palmitate |
| Butyl Paraben | Octyl Palmitate |
| Diazolidinyl Urea | trisodium and tetrasodium edetate (EDTA) |
| Imidazolidinyl Urea | |

PHARMACEUTICAL PRESERVATIVES

| | |
|---|---|
| Ammonia Anhydrous | Potassium Persulfate |
| Ammonium Persulfate | Potassium Sorbate |
| Benzoic Acid | Potassium Sulfite |
| Benzoyl Chloride | Propyl Hydroxybenzoate |
| Butyl Hydroxybenzoate | Propyl Paraben |
| Butyl Paraben | Propylene Glycol |
| Calcium Ascorbate | Saccharin |
| Calcium Fluoride | Salicylic Acid |
| Ethanol | Sodium Acetate |
| Ethyl Hydroxybenzoate | Sodium Ascorbate |
| Ethyl Paraben | Sodium Benzoate |
| Formaldehyde | Sodium Bifluoride |
| Formalin | Sodium Bisulfite |
| Hydrofluosilicic Acid | Sodium Chloride |
| Isopropanol | Sodium Chromate |
| Lactic Acid | Sodium Erythorbate |
| Maleic Acid | Sodium Fluoride |
| Maleic Anhydride | Sodium Nitrate |
| Methyl Hydroxybenzoate | Sodium Silicofluoride |
| Methyl Paraben | Sodium Sulfite |
| Pine Oil | Sorbic Acid |
| Potassium Benzoate | Stannous Chloride |
| Potassium Bifluoride | Stearic Acid |
| Potassium Metabisulfite | Sulfur Dioxide |
| Potassium Nitrate | Zinc Chloride |

As used herein the term "prophylaxis" refers to preventing or reducing the risk of acquiring or transmitting sexually transmitted diseases. In addition, the term refers to inhibiting the growth or replication of HIV transmitted by sexual contact, for example.

One method of the present invention involves preventing the transmission of HIV vaginally or rectally by contacting a bodily fluid suspected of containing HIV with an aqueous composition having at least one component selected from the group consisting of polyquaternium, glycerin and a preservative system. In a typical embodiment, the bodily fluid is semen. In addition, the method can comprise placing an effective amount of the composition on a penis or in a vagina or rectum within one hour of commencement of sexual contact. Ideally, the composition should be placed before the sexual contact has begun. In one embodiment an effective amount of the composition is 1 ml. One convenient feature of the invention is that the composition can be placed with an applicator. As used herein the term "applicator" refers to a device such as, but not limited to a douche or syringe with an elongated neck, sufficient to comfortably reach inside the vagina or rectum and deposit an effective amount of the composition. Alternatively, the composition can be first combined with a device such as a suppository, condom, sponge or other barrier device, and then inserted into the vagina or rectum or cover the penis as appropriate. Preferable compositions used in the present methods include AstroGlide®, Vagisil® or ViAmor®.

Other methods of the present invention involve methods of prophylaxis of HIV transmission vaginally or rectally by contacting a bodily fluid suspected of containing HIV with a composition having at least one component selected from the group consisting of polyquaternium, glycerin and a preservative system.

In addition, the invention provides methods for reducing the risk of transmission of HIV vaginally or rectally by contacting a bodily fluid suspected of containing HIV with a composition having at least one component selected from the group consisting of polyquaternium, glycerin and a preservative system.

Finally, the invention provides a method for inhibiting the transmission of a sexually transmitted disease caused by an agent present in a bodily fluid, by placing a composition having at least one component selected from the group consisting of polyquaternium, glycerin and a preservative system in a vagina, rectum, condom, sponge or on some other barrier device that can be inserted into a vagina or rectum, prior to the deposition of the bodily fluid into the vagina or rectum. In one embodiment, the agent is HIV, in another embodiment, the bodily fluid is semen and in another the preservative system is methylparaben and propylparaben.

The following examples are intended to illustrate but not limit the present invention.

EXAMPLE I

Preparation of Reagents

A. Specimens

Seminal fluids are collected from normal males. Samples are stored at 4° C. for 1 to 2 days or alternatively stored at −20° C. for up to three months before use. University of Texas Institutional Review Board Approval Guidelines, including informed consent were followed for all samples collected.

B. Viruses

Stocks of 213, AC0–1 and 9H strains of HIV were propagated in human H9 lymphocytes using the standard procedure described in Baron et al., *Arch. Intern. Med.* 159(3):303–310 (1999) and Williams et al., *Virology* 184(2):723–728 (1991), each of which is incorporated herein by reference. Aliquots were stored frozen at −70° C. The Indiana strain of vesicular stomatitis virus (VSV) was propagated in murine L cells using the method in Coppenhaver et al., *New Eng. J. Med.* 330(18):1314–1315 (1994), which is incorporated herein by reference. VSV stocks were stored frozen at −70° C.

C. Cells

Human peripheral blood mononuclear leukocytes (PBL or PBML) and the human lymphocyte cell line, CEM, were prepared and propagated in RPMI 1640 medium containing 10% fetal bovine serum and antibiotics, as described in Baron et al., *Arch. Intern. Med.*, supra. Human peripheral blood macrophages were obtained by Ficoll-Hypaque purification of normal peripheral blood leukocytes. To obtain macrophages, the purified PBL were allowed to adhere to a glass surface for three hours at 37° C. Unattached mononuclear leukocytes were rinsed away with medium and the adherent macrophages used in the experiments involving cell viability in the presence of saliva. Human CEM lymphocytes and THP-1 macrophages were propagated by established procedures, reported in Baron et al., *Arch. Intern. Med.*, supra.

EXAMPLE II

Virus Multiplication

The effect of various treatments on virus multiplication was determined in virus-infected human CEM lymphocytes, THP-1 macrophages peripheral blood mononuclear leukocytes, or L929 cells. The multiplication of HIV in PBLs was determined as the yield of infectious HIV from $2 \times 10^6$ Ficoll-Hypaque purified normal peripheral blood mononuclear cells that had been cultured with phytopemagglutinin (4 ug/ml) for 2 days before treatment with 20 u/ml of interleukin 2 (40 units/ml) for an additional 2 days and then infected with $10^5$, 50% tissue culture infectious doses of HIV, strain 213. The infected cells were then incubated with 20 u/ml interleukin 2 for five days, washed four times, and then incubated with or without samples, the various mixtures of samples, or culture medium for 15 o 60 minutes. These leukocytes were subsequently washed and cultured for HIV production in RPMI 1640 tissue culture medium, plus 15% fetal bovine serum and 20 u/ml of interleukin 2 for 24 hours before harvesting the cell-free medium for assay of HIV yield as described according to the assays described in EXAMPLE III. In experiments using the human CEM lymphocyte cell line, described in McKeating et al., *J. Gen. Virol.* 80(12):3327–3333 (1989), which incorporated herein by reference, multiplication was determined as the yield of infections HIV from $6 \times 10^5$ CEM lymphocytes that were infected with $10^5$, 50% tissue culture infections doses of HIV strains. The cells were then incubated for four days and washed four times before 15 to 60 minute treatments with the various preparations. These infected lymphocytes were subsequently washed four times and cultured for 24 hours before harvesting for assay of HIV production as described in EXAMPLE III. For experiments requiring non-containment facilities to perform more complex procedures, a substitute safer surrogate virus, vesicular stomatitis virus (VSV) was used in place of HIV. Other surrogate viruses have been used previously, as described in Baron et al., *Arch. Intern. Med.*, supra. VSV multiplication are measured similarly as the yield of infectious virus in the culture medium from the CEM lymphocytes, THP-1 macrophages, or murine L cells. This is done following infection with 3,000 viral plaque-forming units. Pilot experiments were done initially using VSV-infected human CEM lymphocytes, THP-1 macrophages or murine L cells. Confirmatory experiments were done using HIV-infected CEM lymphocytes and peripheral blood mononuclear leukocytes. All studies were replicated three times.

EXAMPLE III

Assays of HIV and VSV Production

The production of HIV in the experiments was determined by the standard tissue culture infectious dose 50% assay using MT-2 human lymphocytes, as described in McKeating et al., supra. Specifically, the culture fluids harvested from the HIV-infected human cells were serially diluted in 0.5 $\log_{10}$ increments using RPMI culture medium containing 10% fetal bovine serum. 50 ul of each dilution was added to quadruplicate microtiter wells, each containing 110 ul of $2 \times 10^4$ MT-2 cells in culture medium. After the serial dilutions, 120 ul of nutrient medium was added to each well. These microtiter plates were then incubated at 37° C. for three days in a $CO_2$ incubator, and then re-fed culture medium containing 10% fetal bovine serum. The wells were read for HIV multinucleated giant cell cytopathic effect on day 5 or 6. The 50% tissue culture infections dose was determined using the Reed-Muench method, as described in Reed et al., *Am. J. Hyg.* 27:493–497 (1938), which is incorporated herein by reference. The production of VSV was determined as plaque-forming units in L cells.

In addition to basic descriptive statistics, e.g. the Student T Test, statistical methods such as regression analysis and nonparametric methods were used, with no adjustments for multiple testings. In the past, in every instance the pertinent trends and differences observed were large and all related significance levels (P values) were small, even with sample sizes used.

EXAMPLE IV

VSV Inhibition with Vaginal Preparations in Seminal Fluid

This example provides evidence that over the counter vaginal preparations can inhibit multiplication of vesicular stomatitis virus (VSV) in seminal fluid. As show in FIG. 1, commercially available vaginal preparations, including AstroGlide® and Vagisil®, as well as Nonoxynol-9® were tested for their effectiveness in inhibiting the multiplication of VSV. For example, VSV infected CEM lymphocytes were exposed to AstroGlide® and the $\log_{10}$ inhibition of multiplication recorded. VSV was chosen in this experiment since it has similar kinetic and structural properties to HIV, but is considerably more safe and practical to handle in a laboratory. Greater than 10,000 fold inhibition was observed, both when AstroGlide® was mixed with the cells and when it was merely layered on. Nonoxynol-9® showed an almost identical degree of inhibition. Only Vagisil® showed a slightly less inhibition when it was mixed with the cells. Although Nonoxynol-9® exhibits strong inhibitory properties, its use in vivo is impractical due to its propensity to cause mucosal inflammation, which may be the cause of its ineffectiveness in human clinical trials.

Figure 1:
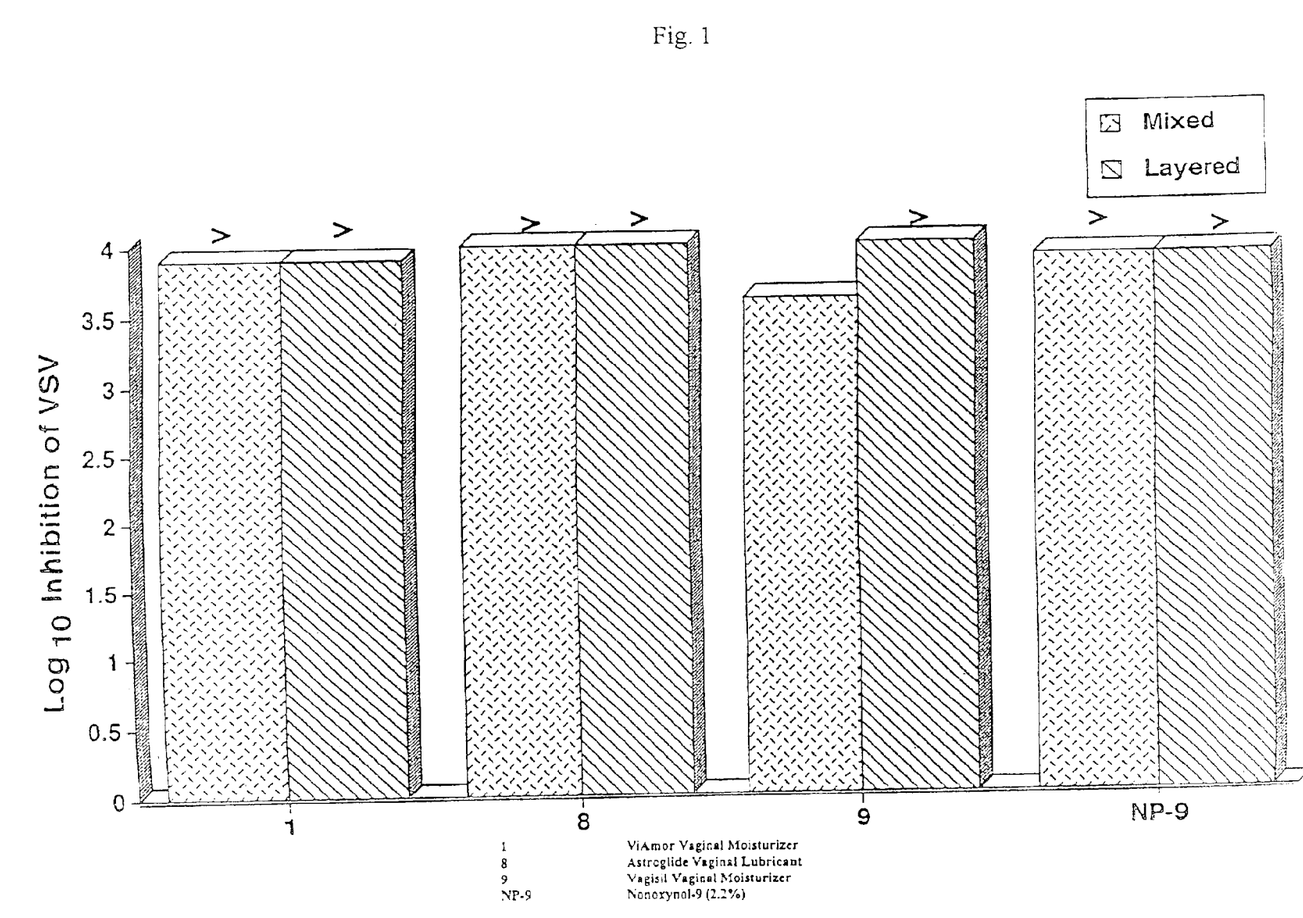
FIG. 1 is a graphical representation of the effectiveness of over the counter vaginal preparations at inhibiting VSV multiplication in CEM lymphocytes in seminal fluid.

These results demonstrate that the compositions of the methods of the invention, including without limitation AstroGlide® and Vagisil®, can penetrate seminal fluid sufficiently to reach cells infected with the virus and can kill those cells preventing multiplication and production of the virus.

EXAMPLE V

HIV Inhibition with Vaginal Preparations in Seminal Fluid

Following the observation that the vaginal preparations above strongly inhibit VSV multiplication in seminal fluid, an experiment under similar conditions using HIV was performed.

Figure 2:
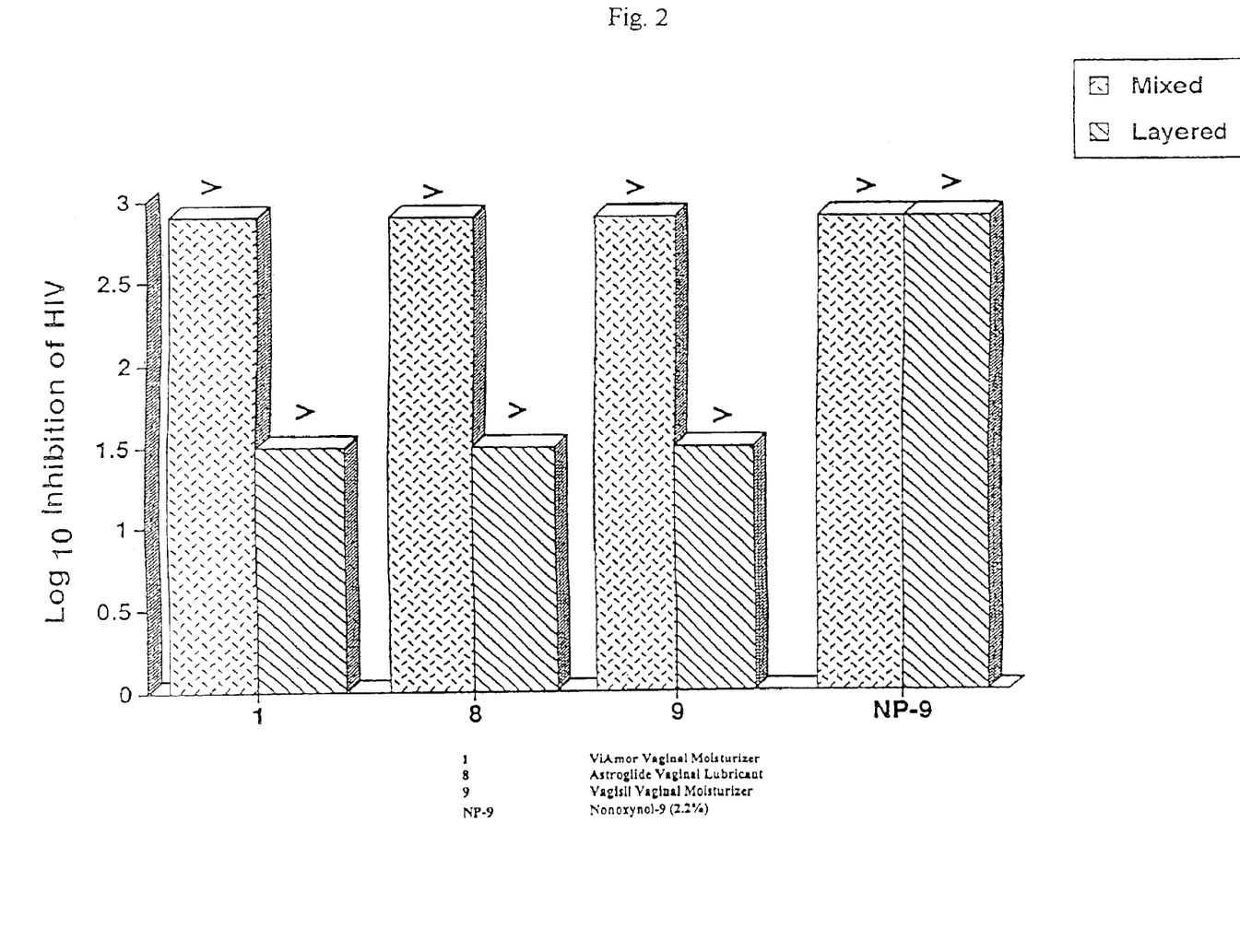
FIG. 2 represents the effectiveness of over the counter vaginal preparations at inhibiting HIV multiplication in human CEM lymphocytes in seminal fluid.

As shown in FIG. 2, AstroGlide® and Vagisil® strongly inhibit the multiplication of HIV infected CEM lymphocytes in seminal fluid. For example, when the preparations were mixed with the seminal fluid, each of the preparations showed greater than a 1,000 fold inhibition. As expected, when the preparations were layered on, they produced greater than 30 fold inhibition. Interestingly, Nonoxynol-9® resulted in greater than 1,000 fold inhibition both when mixed and layered on.

These results confirm that the compositions of the methods of the invention, including without limitation Astro-Glide® and Vagisil® are extremely effective at inhibiting the multiplication of HIV infected CEM lymphocytes in seminal fluid.

EXAMPLE VI

Time Studies of Vaginal Preparations for HIV Inhibition

This example identifies the time required for the compositions of the methods of the invention, and in particular, vaginal preparations to inhibit production of HIV by infected CEM lymphocytes.

Figure 3:
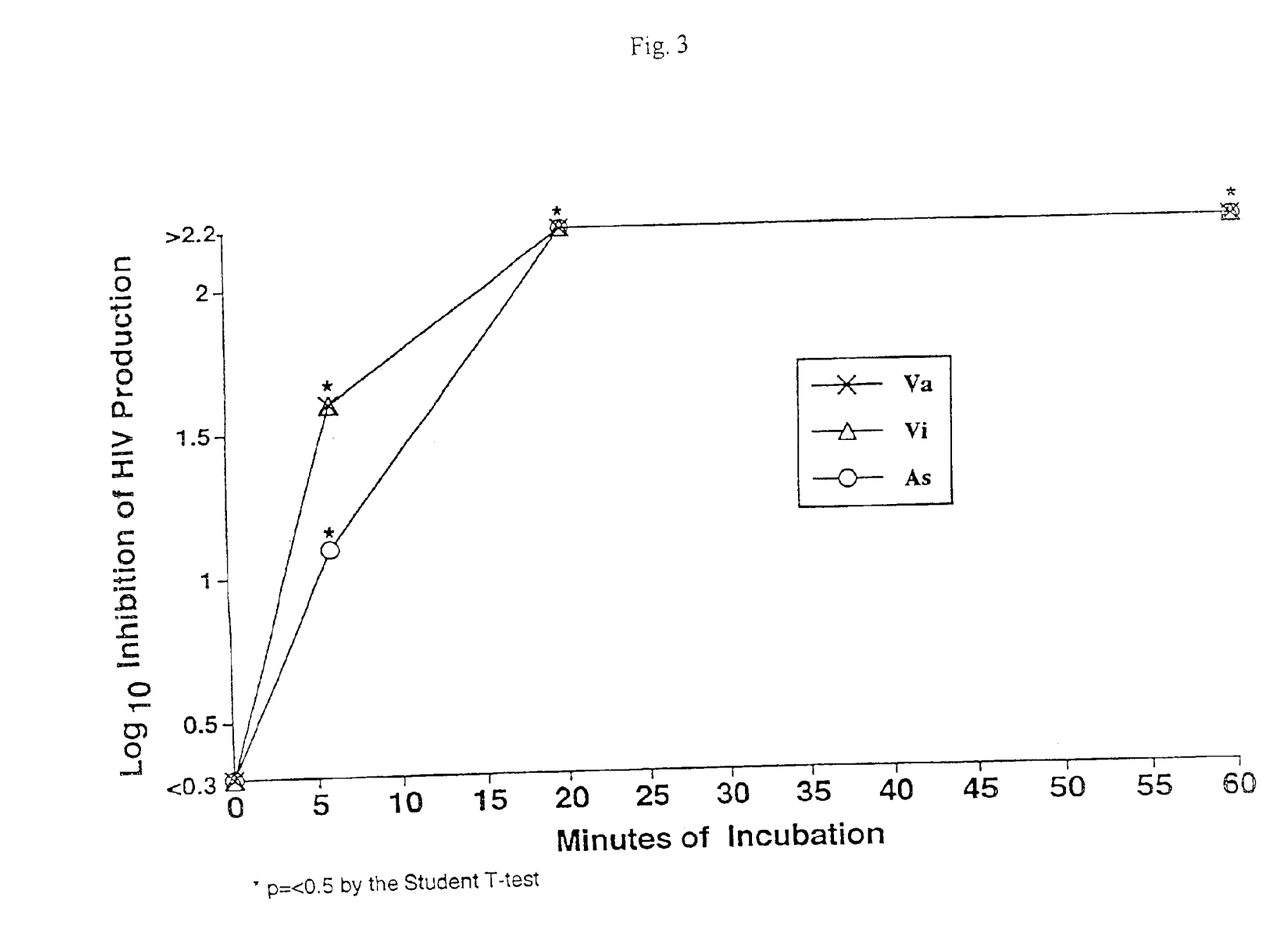
FIG. 3 shows the time required for over the counter vaginal preparations to inhibit production of HIV by infected human CEM lymphocytes.

As seen in FIG. 3, the vaginal preparations began to act within 5 minutes and within 20 minutes of incubation they produced a maximal level of inhibition of greater than 100 fold. This level of inhibition remained steady for at least 60 minutes.

As described previously herein, it has been demonstrated that HIV infected lymphocytes and HIV in cell-free form can remain in seminal fluid inside a vagina or rectum for up to one hour before the virus enters the recipients epithelial tissue, assuming no trauma to the surrounding epithelial tissue has occurred. Accordingly, these results show that timely placing the compositions of the invention in the vagina or rectum after sexual contact would destroy HIV before it could be transmitted in this manner.

EXAMPLE VII

Inhibition of Cell Free HIV by Vaginal Preparations

This example demonstrates the ability of the compositions of the methods of the invention to inhibit cell-free HIV. It is generally reported by the scientific literature that in seminal fluid, most HIV is found sequestered in cells, with a ratio of 10 HIV sequestered to 1 free HIV. Accordingly, the ability of the vaginal preparations to inhibit cell-free HIV was studied as well.

Figure 4:
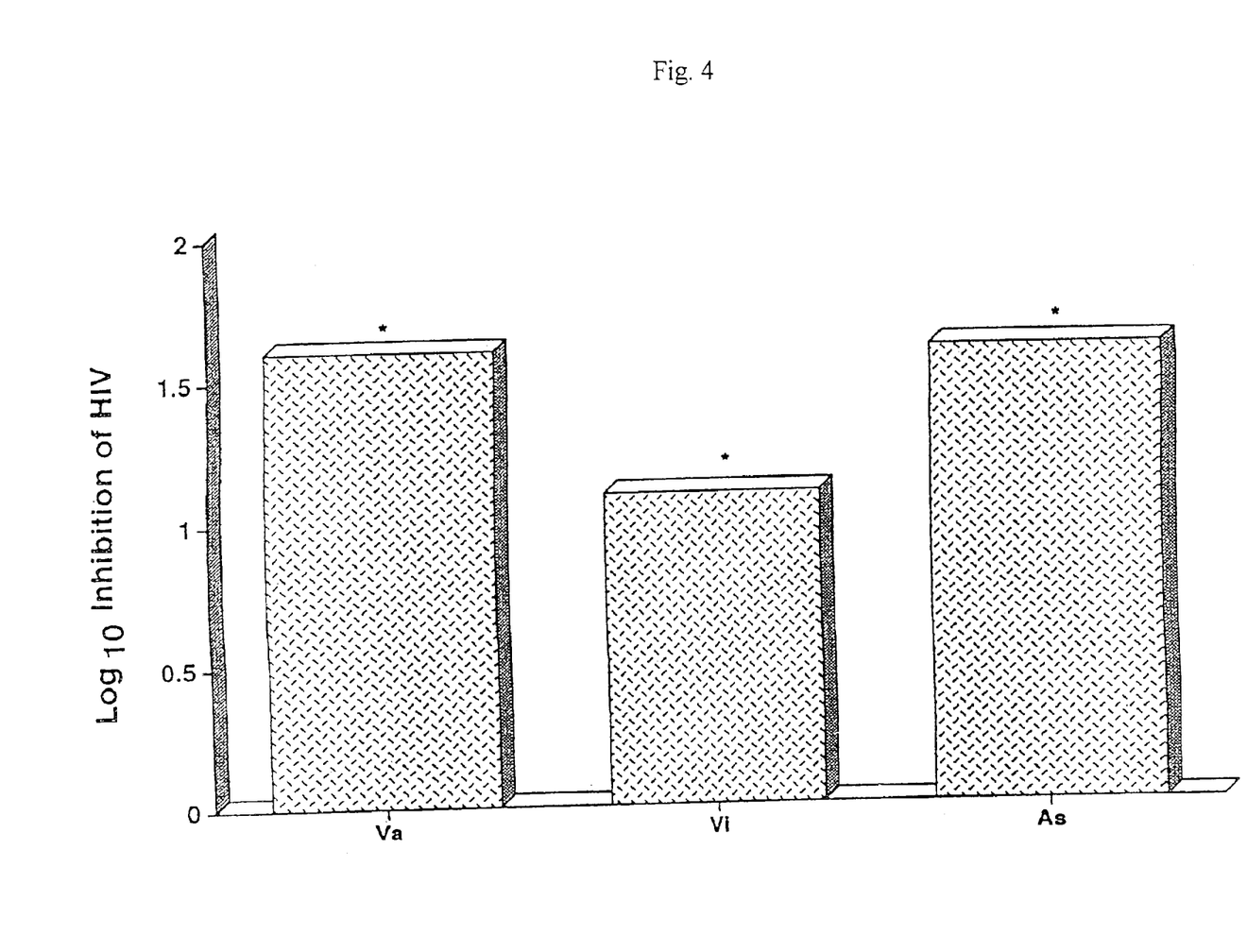
FIG. 4 shows the effectiveness of over the counter vaginal preparations at inhibiting the multiplication of cell-free HIV.

As shown in FIG. 4, the vaginal preparations AstroGlide® and Vagisil® produced a significant inhibition of cell-free HIV. For example, Vagisil® produced an inhibition of approximately 45 fold, while ViAmor® produced approximately 15 fold inhibition and Astroglide® produced approximately 45 fold inhibition of HIV.

Accordingly, these results demonstrate that the compositions of the methods of the invention, including without limitation the over the counter vaginal preparations Astroglide® (ViAmor®), and Vagisil® are highly effective at inhibiting cell-free HIV as well.

EXAMPLE VIII

Inhibition of Cell Free HIV by Vaginal Preparations in Seminal Fluid

This example was performed to determine whether the compositions of the method of the invention would also inhibit cell-free HIV in seminal fluid.

Figure 5:
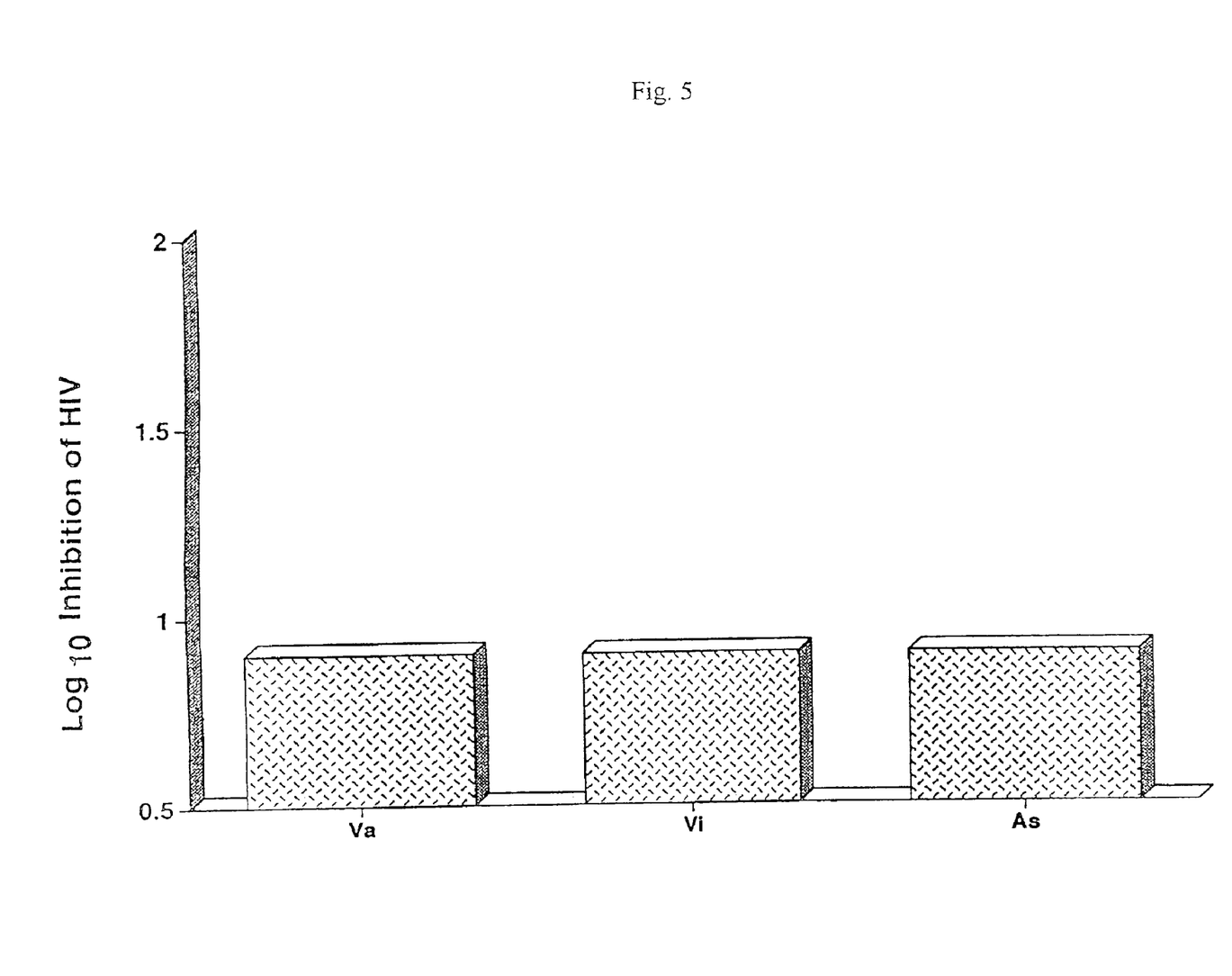
FIG. 5 shows the effectiveness of over the counter vaginal preparations at inhibiting the multiplication of cell-free HIV in seminal fluid.

As shown in FIG. 5, each of the vaginal preparations was effective at inhibiting cell-free HIV in seminal fluid. For example, an inhibition of approximately 6 fold was observed with each of Vagisil® and AstroGlide®. Accordingly, these results demonstrate that the vaginal preparations were able to penetrate the somewhat protective seminal fluid and strongly inhibited cell-free HIV.

EXAMPLE IX

Toxicity and Inhibitory Titers of Vaginal Preparation Components

This example explored the toxicity and inhibitory titers of the various components of the vaginal preparations.

Figure 6:
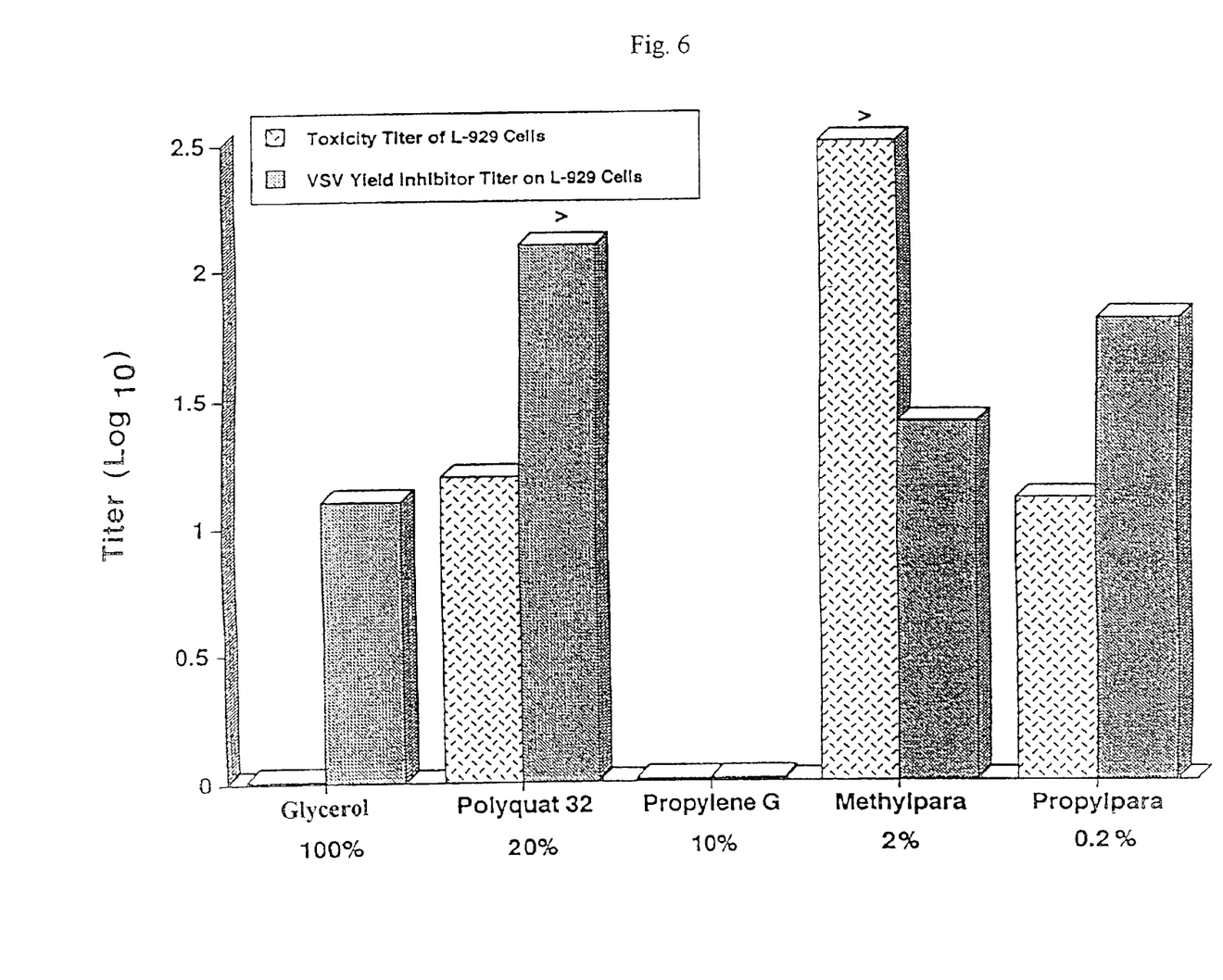
FIG. 6 shows the toxicity and inhibitory titers of components of over the counter vaginal preparations. Toxicity and inhibitory activities of the components were absent in concentrations below 8% glycerol, 0.2% polyquaternium 32, 0.2% methylparaben, and 0.004% propylparaben.

Solutions of the components shown in FIG. 6 were diluted, and the inhibitory and toxicity characteristics of the diluted solutions were evaluated. At an 8% concentration, glycerol was not very effective at killing L-929 cells but produced greater than a 10 fold inhibition of VSV. Polyquaternium 32 at 0.2% concentration produced a greater than 10 fold killing of L-929 cells and a greater than 100 fold inhibition in VSV. Propylene G (propylene glycol) produced almost no inhibition or killing at all. Methylparaben at only a 0.2% concentration produced a greater than 300 fold titer of L-929 cells but produced a VSV inhibition of approximately 30 fold. Proplyparaben at 0.004% produced a L-929 toxicity titer of approximately 15 fold and a VSV inhibition of approximately 55 fold.

Accordingly, glycerol, polyquaternium, methylparaben and proplyparaben each individually were effective at inhibiting VSV, and most likely HIV as well. Further studies will determine if similar effects are seen with HIV and whether the inhibition is cumulative or synergistic.

This example demonstrated that the protection afforded by AstroGlide® was not due to hypotonicity, but was rather due to the inactivation of infected leukocytes by one or more of the compounds comprising Astroglide®. Accordingly, the hypotonic factor of AstroGlide® was not responsible for the inhibition of HIV-infected leukocytes. Therefore, Astro-Glide® had protective chemical compound(s) independent of hypotonicity, and that it was not the lack of salts but one or more chemical compounds which accounted for the inactivation of HIV by the compositions useful in the methods of the invention. Further studies will be performed using the compositions on HIV-infected leukocytes. In further studies, salts are added to create an isotonic condition to further demonstrate that AstroGlide® and the compositions of the method of the invention retain highly protective properties even when present or dissolved in an isotonic environment.

EXAMPLE X

Inhibitory Action in Multiple Strains of HIV

This example demonstrates that compounds of the methods of the invention strongly inhibit multiple strains of HIV. Three additional HIV isolate strains, 213, AC-1 and 9H, are used to infect human CEM lymphocytes suspended in seminal fluid. Stocks of the 213, Ac-1 and 9H strains of HIV are propagated in human H9 lymphocytes using the standard procedure described in Baron et al., *Arch. Intern. Med.*, supra and Williams et al., *Virology* 184(2):723–728 (1991), both of which are incorporated by reference herein. Two groups of infected cells are prepared, and one group is treated with, for example, AstroGlide® and the other is not. It is determined that AstroGlide® strongly inhibits the multiplication of the three HIV strains, Cells that are not treated remain viable. The results confirm the general applicability of the protection AstroGlide® among the compounds of the methods of the invention provides against multiple strains of HIV, which has utility for HIV infection in humans.

EXAMPLE XI

Studies with HIV-Infected Monocytes

Since HIV infects monocytes as well as lymphocytes in human seminal fluid, the following experiment are performed to determine whether the compounds of the methods of the invention, including AstroGlide®, can protect against HIV-infected monocytes as well as lymphocytes. THP-1 monocytes are suspended in seminal fluid. Two groups of cells are prepared. One group is treated with AstroGlide® and the other group is not. The results show that AstroGlide® strongly inhibits HIV-infected monocytes. Therefore, the findings demonstrate that AstroGlide® can protect against all types of HIV-infected leukocytes in seminal fluid.

EXAMPLE XII

Studies with Primary Cells

This example is performed to demonstrate whether the compounds of the methods of the invention, including AstroGlide®, could provide protection against HIV-infected primary peripheral blood leukocytes. Human seminal fluid normally contains primary peripheral blood leukocytes rather than the cell lines used in previous studies. Normal human peripheral blood mononuclear leukocytes are purified from human blood, according to established protocols, which are known to those skilled in the art. Next, they are suspended in seminal fluid, infected with HIV and then treated or not with AstroGlide®. The results demonstrate that AstroGlide® is highly effective at inhibiting HIV-infected primary peripheral blood leukocytes. Therefore, these findings are applicable to human therapy.

EXAMPLE XIII

Inactivation of Cell-Free HIV Strains

This example is performed to determine whether compounds of the method of the invention, including AstroGlide®, inactivate four strains of cell-free HIV. Four strains of cell-free HIV suspended in seminal fluid are treated or not treated with AstroGlide®. The results demonstrate that AstroGlide® inactivates all strains of cell-free HIV greater than 90%. Accordingly, AstroGlide® is protective against cell-free as well as HIV-infected cells.

EXAMPLE XIV

Protection Against Sexually Transmitted Agents

This example is performed to determine whether compounds of the methods of the invention, including AstroGlide®, provide protection against sexually transmitted agents, other than HIV, as well. For example, the agent of herpes is herpes simplex virus (HSV). In order to test the protection against HSV, Vero cells are suspended in seminal fluid. AstroGlide® is added to the cells. The cells are assayed according to procedures described previously herein. The results demonstrate that AstroGlide® strongly inhibits HSV as well. Accordingly, they provide protection against herpes transmission.

The compositions of the method of the invention, including AstroGlide®, are also tested for their ability to inhibit the Papilloma virus through study of its virus family, Papoviruses. Protection against the genital strain of Papovirus is studied in infected cells and cell-free virus suspended in seminal fluid. AstroGlide® is added to the culture. The cells are then assayed according to the procedure described previously herein. The results demonstrate that AstroGlide® strongly inhibits the genital strain of papovirus. Accordingly, they provide protection against genital wart transmission.

AstroGlide® and the other compositions are additionally tested for their ability to inhibit other sexually transmitted microbes, such as gonorrhea, syphilis, chlamydia and mycoses. To determine the protective effect against these microbes, each organism is cultured in nutrient medium according to procedures that are well known to those skilled in the art. The cultures are either treated or not treated with AstroGlide® at systematically varying concentrations, all of which can be determined by those skilled in the art, and which are further described in Baron et al., *Medical Microbiology*, $4^{th}$ ed., Galveston Tex., The University of Texas Medical Branch at Galveston, (1996), which is incorporated herein by reference. The results demonstrate that AstroGlide® is highly effective at destroying these organisms, as indicated by the antimicrobial titer. In addition, they provide protective action.

EXAMPLE XV

Persistence Studies

This example demonstrates the duration of anti-HIV activity of the compositions of the method of the invention, including AstroGlide®, in the vagina and rectum.

Five rabbit vaginas are treated with AstroGlide® and sampled at four hours. Additionally, five rabbit rectums are treated with AstroGlide® and sampled at four hours. These rabbits will have been placed on a water-only diet for 12 hours prior to testing. The recovered samples are tested for anti-HIV activity in comparison with the original preparations. The results demonstrate that AstroGlide® retains high anti-HIV activity even after four hours. Accordingly, AstroGlide® is useful in practice.

EXAMPLE XVI

Human Studies

This example demonstrates the ability of AstroGlide® and the compositions of the methods of the invention to provide protection against HIV in humans. It further explores the duration of that protection.

The following is performed according to standard human subject protocol and is subject to Institutional Review Board approval. Women are provided with stocks of AstroGlide®, which is subsequently placed in the vagina. After four hours, aliquots are removed and tested for anti-HIV activity. In addition, either fasting men or women have AstroGlide® placed in the rectum. Samples are also removed at four hours and tested in a similar fashion. The results demonstrate that AstroGlide® retains high anti-HIV activity after four hours in the body. Accordingly, AstroGlide® is useful for human application.

Although the invention has been described with reference to the examples provided above, it should be understood that various modifications can be made without departing from the spirit of the invention. Accordingly, the invention is limited only by the following claims.

We claim:

1. A chemical method for reducing the risk of HIV transmission in the vaginal or rectal lumen, said method comprising the step of contacting semen suspected of containing HIV with about 0.5 ml to about 10 ml of an aqueous gel composition consisting essentially of:

from about 0.1% to about 10% by weight polyquaternium;

from about 5% up to 60% by weight glycerol;

from about 0.03% to about 3% by weight of a preservative system, said preservative system having at least two preservatives, and the balance water, wherein said aqueous composition is deposited in said lumen within about four hours of the commencement of sexual contact.

2. The method of claim 1 wherein said aqueous gel composition consists essentially of:

from about 0.1% to about 10% by weight polyquaterniuin;

from about 5% up to 60% by weight glycerol; and from about 0.03% to about 0.3% methylparaben and about 0.015% to about 0.15% by weight propylparaben.

3. The method of claim 1 wherein said preservative system consists essentially of methylparaben and propylparaben.

4. The method of claim 1 wherein said aqueous gel composition is selected from the group consisting of vaginal lubricants and personal lubricants.

5. The method of claim 4 wherein said composition is Astroglide (tm) or Vianior (tm).

6. The method of claim 1 wherein the depositing of aqueous gel in the vaginal or rectal lumen is before or after sexual contact.

7. The method of claim 1 wherein the aqueous gel composition is placed in the vagina or rectum using an applicator.

* * * * *